United States Patent [19]

Borody

[11] Patent Number: 5,196,205
[45] Date of Patent: Mar. 23, 1993

[54] METHOD FOR TREATMENT OF GASTRO INTESTINAL DISORDERS

[76] Inventor: Thomas J. Borody, 144 Great North Rd., Five Dock, Australia, 2046

[21] Appl. No.: 466,310
[22] PCT Filed: Sep. 29, 1988
[86] PCT No.: PCT/AU88/00379
§ 371 Date: Jun. 12, 1990
§ 102(e) Date: Jun. 12, 1990
[87] PCT Pub. No.: WO86/05981
PCT Pub. Date: Oct. 23, 1986

[30] Foreign Application Priority Data

Oct. 12, 1987 [AU] Australia ............................. PI4838
Dec. 18, 1987 [AU] Australia ............................. PI5985
Mar. 30, 1988 [AU] Australia ............................. PI7513

[51] Int. Cl.$^5$ ................. A01N 59/16; A01N 37/18; A01N 13/50; A61K 31/43
[52] U.S. Cl. ................................. 424/653; 514/154; 514/199; 514/398; 514/925
[58] Field of Search ............... 424/653; 514/925, 53, 514/54, 398, 152, 199, 154

[56] References Cited

U.S. PATENT DOCUMENTS

4,935,406  6/1990  Coleman ............................. 514/54

OTHER PUBLICATIONS

Lambert, J. R., et al., Colonization of Gnotobiotic Piglets with Gampylobacter Pyloridis, Gastroenterology 92, 1489 (May 1987).
Borsch, G., et al., Gastroenterology, vol. 94, No. 5, part 2, A44 (May 1988).
Borody, T., et al., Gastroenterology, vol. 94, No. 5, Part 2, A43 (May 1988).
Lambert, J. R., et al., Effect of Colloidal Bismuth (DE-Nol) on Healing and Relapse of Duodenal Ulcers—Role of Campylobacter Pyloridis, Gastroenterology 92, 1489 (May 1987).
Borody, T. J. et al., The Medical Journal of Australia, vol. 146, pp. 450-451 Apr. 20, 1987.

Blaser, M. J., et al., The New England Journal of Medicine, 1444-1452 Dec. 10, 1981.
Marshall, B. J., et al., The Medical Journal of Australia, vol. 142, 439-444 Apr. 15, 1985.
McNulty, C. A. M., et al., The Lancet, 1068 May 12, 1984.
Marhsall, B. J., et al., The Lancet 1311-1315 Jun. 16, 1984.
Marshall, B. J., et al., The Lancet, 281 Aug. 4, 1984.
Koo, J. Ho, et al., Gastroenterology, 864-870 May 1982.
Steinhoff, M. C., et al., Gastroenterology, 78(6), 1495-1499 Jun. 1980.
McNulty, C. A. M., et al, British Medical Journal, 293, 645-649 Sep. 13, 1986.
The Lancet, Jun. 7, 1986, pp. 1306-1307.
Hislop, I., et al, Gastroenterological Society of Australia, Dec. 1984, p. 907.
Walan, A., Non-Ulcer Dyspensia, Proceedings of a Symposium Held in Stockholm, Nov. 6/7, 1981, cover contents, preface pages.
Misiewicz, J. J., et al, Diseases of the Gut and Pancreas, 1987, Chapter by J. R. Bennet, p. 16.
Misiewicz, J. J., et al, Diseases of the Gut and Pancreas, 1987, chapter by La Brooy, S. J., p. 239.
Romaniuk, P. J., et al, Journal of Bacteriology, 169, No. 5, May, 1987, pp. 2137-2141.
Goodwin, S., et al., *C. Pylori* Symposium, Keystone, Colorado., Jul. 1987, Abstract page.

(List continued on next page.)

*Primary Examiner*—Frederick E. Waddell
*Assistant Examiner*—Gregory Hook
*Attorney, Agent, or Firm*—Ronald P. Kananen

[57] ABSTRACT

A method is disclosed for preventing recurrence of duodenal ulcer associated with *Campylobacter pylori* infection in a patient suffering from duodenal ulcer disease associated with *Campylobacter pylori* infection by administering a pharmaceutically acceptable bismuth compound; a first antibiotic selected from the group consisting of tetracycline and penicillins and second antibiotic which is metronidazole.

3 Claims, 1 Drawing Sheet

OTHER PUBLICATIONS

American Illustrated Medical Dictionary, W. B. Saunders Company, 1951, p. 501.

Gentleman, 1951, p. 83.

Clinics in Gastroenterology, vol. 13, No. 2, May 1984, pp. 437–446 (by Lagarde, S. P. et al.).

Marshall, B. The Lancet, Jun. 4, 1983, pp. 1273–1275.

Langenberg, M. L., et al, The Lancet, Jun. 16, 1984, pp. 1348–1349.

PDR, p. 646, undated; on Pepto-Bismol ®.

Specialties, p. 212 (undated).

Piper, D. W., "Bacteria, gastritis, acid hyposecretion and peptic ulcer," The Medical Journal of Australia, 142, No. 8, Apr. 15, 1985, 431.

Marshall, B. J., et al., "Attempt to fulfill Koch's postulates for pyloric campylobacter," The Medical Journal of Australia, 142, No. 8, Apr. 15, 1985, 436–439.

Jones, D. M., et al Campylobacter III, Proceedings of the Third International Workshop on Campylobacter Infection, Jul. 7–10, 1985, Abstract No. 097, pp. 161–162.

Langenberg, M. L., et al, Campylobacter III, Proceedings of the Third International Workshop on Campylobacter Infection, Jul. 7–10, 1985, Abstract No. 098, pp. 162, 163.

Bartlett, J. G., Gastroenterology, 94, 229–232 (1988).

Graham, J., The Medical Journal of Australia 148, 104 Jan. 1988.

Nyren, O., et al, The New England Journal of Medicine 314, No. 6 pp. 339–342 (Feb. 1986).

Talley, N. J., J. Clin. Gastroenterol 10(1), 10–12 (1988).

Marhsall, B. J., The Journal of Infectious Diseases, vol. 153, No. 4, pp. 650–657 (Apr. 1986).

Rathbone, B. J., et al, The Lancet, p. 398 (Aug. 15, 1987).

Michel, J., et al, Antimicrobial Agents and Cheotherapy, vol. 23, No. 5, pp. 796–797 (May 1983).

McNulty, C. A. M., Antimicrobial Agents and Chemotherapy, vol. 28, No. 6, pp. 837–838 (Dec. 1985).

Kasper, G., et al, Immunitat und Infektion, vol. 14, No. 2, pp. 58–62 (Apr. 1986).

Goodwin, C. S., J. Clin. Pathol. vol. 39, pp. 353–365 (1986).

McNulty, C. A. M., et al, Campylobacter III, Proceedings of the Third International Workshop of Campylobacter Infection, Jul. 7–10, 1985, Abstract No. 099, pp. 163–164.

Marshall, B. J., et al, Campylobacter III, Proceedings of the Third International Workshop on Campylobacter Infection, Jul. 7–10, 1985, Abstract No. 100, pp. 165–166.

Lambert, J. R. Gastroenterology, 88, No. 5, p. 1462 (1985).

Axon, A. R., BMJ, vol. 302, Apr. 20, 1991, 919–921.

Axon, A. T. R., Journal of Gastroenterology and Hepatology (1991)6, 131–137.

Borody, T. J. et al, The Medical Journal of Australia, 151, 431–435 (Oct. 16, 1989).

Borsch, G. et al, Gastroenterology, vol. 94, No. 5, Part 2, A44 (May 1989).

Burette, A. et al, Gastroenterology 98 (S) II: A26 (1990).

Burette, A. et al, Gastroenterology 98 (S) II: A27 (1990).

Carrick, J. et al, Rev. Esp. Enf. Digest, vol. 78, 122–123 (Nov. 1990).

Coelho, L. G. V. et al, Am. J. Gastro., vol. 85:1231, 1990.

Coghlan, J. G. et al, The Lancet, Nov. 14, 1987, 1109–1111.

Coghlan, J. et al, Aliment. Pharmacol. Therap. (1990) 4, 49–54.

DeKoster, E. et al, Gastroenterology, 1990, 98(S) II, A35.

Daskalopoulos, G. et al, Rev. Esp. Enf. Digest, vol. 78, p. 113 (1990).

DeKoster, E. et al, Rev. Esp. Enf. Digest, vol. 78, 118–119 (Nov. 1990).

George, L. J. et al, The medical Journal of Australia, 153, 145–149 (Aug. 6, 1990).

Glupczynski, Y. et al, The American Journal of Gastroenterology, 83:365–372, (1988).

Glupczynski, Y. et al, The American Journal of Gastroenterology, 85, No. 12, 1545–1551 (1990).

Graham, D. Y. et al., Gastroenterology May, 1989, 96:A 181.

Graham, D. Y. et al, Rev. Esp. Enf. Digest, vol. 78, p. 117 (Nov. 1990).

Hirschl, A. M. et al, European Journal of Gastroenterology and Hepatology 1991, vol. 3, No. 1, pp. 3–7.

Kraft, W., Gastroenterology 1988; 95:1178–84.

Lambert, J. R. et al, Rev. Esp. Enf. Digest, vol. 78, pp. 115–116 (1990).

(List continued on next page.)

OTHER PUBLICATIONS

Lamouliatte, H., Rev. Esp. Enf. Digest, vol. 78, p. 101 (1990).
Logan, R. P. H. et al, British Society of Gastroenterology 1991:32:A584.
Logan, R. P. H. et al, Rev. Esp. Enf. Digest, vol. 78, p. 124 (1990).
Marshall, B. J. et al, The Lancet, Dec. 24/31, 1988, pp. 1437–1442.
Misiewicz, J. J. et al, eds., Diseases of the Gut and Pancreas, Blackwell Scientific Publications, Oxford, 1987, pp. 288–315.
Patchett, S. et al, The British Society of Gastroenterology, 31, A1199–A1200 (1990).
Ramaker, J., European Journal of Gastroenterology and Hepatology, 1990, vol. 2 (Supp. 1), 1987.
Rauws, E. A. J. et al, Gastroenterology 1988:94: 33–40.
Rauws, E. A. J. et al, The Lancet, vol. 335 1233–1235 (May 26, 1990).
Scheig, R., The American Journal of Gastroenterology, 85, No. 12, 1552–1556 (1990).
Unge, P. et al, Scand. J. Gastroenterol. 1989, 24 (Suppl. 167), 49–54.
Wagner, S., Rev. Esp. Enf. Digest., vol. 78, pp. 116–117 (Nov. 1990).
The Washington Post, Health, p. 6, May 28, 1991.
World Congress of Gastroenterology, Sydney, Australia, Aug. 26–31 1990, transcripted typed from tape.
Lee, A., Today's Life Science, 12–24 (Nov. 1990).
Sunday telegraph (Australia), Jun. 2, 1991.
Goodwin, C. S., et al, Current Science, 108–115 (1991).
Lee, F. I., et al, Gut, 32, 151–153 (1991).
McNulty, C. A. M., pp. 195–207, from Campylobacter pylori in Gastritis and Peptic Ulcer Disease (M. J. Blaser, ed.), Iqaku-Shoin, New York, 1989.
Borody, T. J., et al, Medical Journal of Australia, vol. 146, pp. 450–451 (May 20, 1987).

METHOD FOR TREATMENT OF GASTRO INTESTINAL DISORDERS

TECHNICAL FIELD

This invention relates to pharmaceutical compositions and therapeutic methods for eradication and/or prevention of recurrence of gastrointestinal disorders associated with infection by *Campylobacter pylori*

BACKGROUND ART

*C. pylori* is a recently described bacterium found to cause chronic histological gastritis. Its causal role in peptic ulceration is less clear and even less so in non-ulcer dyspepsia. Its role could be more effectively studied if effective therapy for its eradication were devised.

Until recent times, *C. pylori* has been found to be difficult to eradicate using known chemotherapeutic agents. Although many antibiotics can suppress *C. pylori* growth in vitro, in vivo the mucosal concentration appears to be inadequate and penetration of the usual gastric mucus layer poor. Hence, development of an adequate in vivo eradication method for chronic *C. pylori* infection has been difficult. Moreover, adequate prediction of in vivo results cannot be predicted from in vitro work.

European Patent Application No. 206,625 and Australian Patent Application No. 59026/86 describe the use of bismuth together with a single antibiotic for the treatment of *C. pylori*. However, bismuth alone achieves low (30 to 70%) initial clearance rates for *C. pylori* and recurrence of the infection approaches 100% by twelve months post therapy. Bismuth together with a single antibiotic, namely amoxicillin, appears to be relatively effective as a short term means of reducing the symptoms but it is now clear that the use of bismuth together with a single antibiotic frequently fails to eradicate the infection and has a high rate of infection recurrence (Rauws, Erik A. J. et al: Gastro-enterology, 1988; 94: 33–40).

DISCLOSURE OF THE INVENTION

The present inventor has now found that the use of a multi antibiotic therapy not only results in a high initial clearance rate of *C. pylori*, of the order of greater than 90%, but also leads to a high eradication rate where most patients remain free of infection for more than twelve to eighteen months. It now seems that therapeutic success measured at eight weeks biopsy (post treatment) should be termed as clearance only whilst the term "eradication" should be used in the context of patients who remain free of *C. pylori* infection for more than twelve months post treatment.

The present inventor has also found that *C. pylori* is not only associated with gastritis but is also casually associated with peptic ulcer including duodenal, prepyloric, gastric, oesophageal and marginal ulcer and consequently the novel therapy for eradication of *C. pylori* described in the present invention is useful in the treatment of peptic ulcer as well as non-ulcer dyspepsia. Moreover, the novel therapy of the present invention is useful in the treatment of oesophageal reflux, reflux oesophagitis as well as asymptomatic carrier states.

In one broad form the present invention provides a pharmaceutical composition for the treatment of gastro intestinal disorders associated with *C. pylori* infections comprising a pharmaceutically acceptable bismuth compound, a first antibiotic or antimicrobial agent and a second antibiotic or antimicrobial agent.

In a further form the invention provides a sequential pack comprising a first pharmaceutical composition in unit dosage form adapted and presented in said pack for a first administration period of 3 to 36 days, said first composition comprising a pharmaceutically acceptable bismuth compound and a first antibiotic or antimicrobial agent together with a second pharmaceutical composition comprising a second antibiotic or antimicrobial agent in unit dosage form adapted and presented in said pack for a second administration period different from said first administration period.

The invention also provides a sequential pack for the administration of at least two pharmaceutical compositions comprising a first composition which comprises a pharmaceutically acceptable bismuth compound, a first antibiotic or antimicrobial agent and a second antibiotic or antimicrobial agent, in unit dosage form adapted and presented for a first administration period of 3 to 36 days, together with a second pharmaceutical composition which comprises an acid suppressant for ulcer treatment in unit dosage form adapted and presented for a second administration period of 3 to 36 days prior to or overlapping with the initial part of said first administration period.

Preferably, the first antibiotic or antimicrobial agent is selected from one or more of tetracyclines, penicillins, quinolones, cephalosporins, furazolidones, lincosamides, nitrofurantoins and/or polypeptides. Preferably, the second antibiotic or antimicrobial agent is selected from one or more of quinolones, furazolidones, nitrofurantions, metronidazoles, and/or cephalosporins.

More preferably the first antibiotic or antimicrobial agent is selected from tetracyclines and/or penicillins and the second antibiotic is a metronidazole.

The tetracyclines include tetracycline, oxytetracycline, doxycycline, demeclocycline, methacycline and minocycline.

The penicillins include penicillin G, penicillin V, oxacillin, nafcillin, ampicillin, amoxicillin, cloxacillin and carbenicillin.

The metronidazoles include metronidazole and tinidazole.

Rifanpin, trimethoprim and/or nalidixic acid may also be used.

The cephalosporins include cephalexin (Keflex), cefaclor, cephapirin, cephradine and cefadroxil as well as second and third generation cephalosporins.

The polypeptide antibiotics include polymyxin B, bacitracin, colisin sulfate and/or spectinomycin HCl.

Quinolones include ciprofloxacin, norfloxacin and ofloxacin.

Lincosamides include lincomycin and clindamycin.

Whilst it is preferred that the first and second antibiotics or antimicrobial agents are selected from different classes, they may be selected from within the one class. Moreover, a third or more antibiotics may be included in the methodology and compositions of the invention; e.g. amoxicillin, tetracycline and metronidazole. Keflex is also preferably used as one of the first or second antibiotics or as a further antibiotic.

Bismuth compounds suitable in the present invention include those selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth salicylate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. The bismuth useful herein may be administered alone, or in combination with other pharmaceutically-acceptable components, in a bismuth-containing composition. A variety of such compositions containing bismuth salts are commercially-available, including, for example, DeNol, containing tripotassium dicitrato bismuthate (sold by Gist-Brocades N.V.). Noralac, containing bismuth aluminate, alginic acid, and magnesium carbonate (manufactured by North American Pharmaceuticals), Roter bismuth, containing bismuth subnitrate (sold by Roter Laboratories), Fensobar Polvo, containing bismuth subcarbonate among other materials (manufactured by USV Pharmaceutical Corporation), and Pepto-Bismol, containing bismuth subsalicylate (sold by The Procter & Gamble Company).

In a preferred form of the present invention there is provided a method of treating gastro intestinal infections associated with C. pylori which comprises administering an effective amount of a pharmaceutically acceptable bismuth compound in combination with a tetracycline and/or a penicillin and a metronidazole.

In a further aspect of the present invention there is provided a capsule for oral administration to patients suffering from gastro intestinal infections associated with C. pylori wherein said capsule includes a pharmaceutically acceptable bismuth compound together with a first antibiotic and a second antibiotic wherein said capsule is adapted to release said bismuth within the stomach of the recipient and wherein at least said first antibiotic and preferably also said second antibiotic is microencapsulated so that said first and optionally said second antibiotic is released within the gastro intestinal tract after said stomach.

In a preferred form of this aspect of the invention there is provided a capsule containing an effective amount of a pharmaceutically acceptable bismuth compound together with enteric coated micro-spherules of an antibiotic of the tetracycline class or penicillin class which capsule also contains an effective amount of a second antibiotic selected from the metronidazole class which second antibiotic is optionally provided in enteric coated micro-spherule form.

In a further aspect of the present invention the methodology uses the treatment regimen comprising the combination of pharmaceutically acceptable bismuth compound in combination with a first antibiotic and a second antibiotic for between three to twenty-eight days. Preferably the treatment is combined with the administration of an acid suppressant such as an histamine$_2$ antagonist such as cimetidine, ranitidine or famotidine to effect symptomatic relief and ulcer epithelialization. This is followed by the combination of the bismuth and first and second antibiotic therapy. Preferably the histamine$_2$ antagonist is administered for three to twenty-eight days followed by a three to twenty-eight day therapy of the bismuth/antibiotics combination. Other acid suppressants may be used instead of an histamine$_2$ antagonist such as benzimidazole or prostoglandins. Alternatively, the histamine$_2$ blocker or other acid suppressant can be combined with the pharmaceutical composition of the present invention.

The present invention also provides a sequence presented pack suitable for therapy for gastro intestinal disorders associated with C. pylori infection which combines a pharmaceutically acceptable bismuth compound together with a first antibiotic and a second antibiotic and optionally further antibiotics so that said treatment regimen can be adapted for individual patient needs. Optionally the sequence presented pack may also include an initial therapy comprising an acid suppressant such as a histamine$_2$ antagonist or a K/Na ATP-ase inhibitor such as omeprazole and may be combined with mucus disrupting agents such as carbocysteine, n-acetylcysteine, corticosteroids or bisolvon. It should be noted that the pharmaceutical composition comprises at least two antibiotics but further antibiotics may be selectively added in difficult cases or where resistant strains and/or multiple strains present a more resistant problem.

In the composition and methodology of the present invention, preferably from 5 to 5000 mg, more preferably 50 to 250 mg of a pharmaceutically acceptable bismuth compound is used together with from 5 to 10000 mg, more preferably 50 to 500 mg of a first antibiotic together with from 5 to 10000 mg, more preferably 50 to 250 mg of a second antibiotic.

Preferably the invention provides a pharmaceutical composition containing from 50 to 250 mg of a colloidal bismuth in pharmaceutically acceptable form, 50 to 500 mg of tetracycline or a penicillin (e.g. amoxicillin) type antibiotic and 50 to 250 mg of a metronidazole type antibiotic such as metronidazole or tinidazole. Preferably the tetracycline or penicillin is microencapsulated to prevent bismuth chelation at high pH.

In a further aspect the invention provides a sequential pack comprising an antimicrobial pharmaceutical composition in unit dosage form adapted for an administration period of three to thirty-six days, said antimicrobial composition comprising a pharmaceutically acceptable bismuth compound, at least a first antibiotic and at least a second antibiotic, together with a palliative pharmaceutical composition in unit dosage form adapted and presented for a three to thirty-six day administration period prior to, or overlapping with the initial part of the administration period of said antimicrobial pharmaceutical composition wherein said palliative pharmaceutical composition comprises a therapeutic agent such as an acid suppressant, adapted for ulcer treatments.

In a further aspect the invention provides a sequential pack comprising a first pharmaceutical composition in unit dosage form adapted for an administration period of three to thirty six days, said composition comprising a pharmaceutically acceptable bismuth compound and at least a first antibiotic, together with a second pharmaceutical composition in unit dosage form comprising a second antibiotic adapted for administration for a period different to said administration period of said first pharmaceutical composition. Preferably the pack further comprises a palliative pharmaceutical composition in unit dosage form presented in said pack in a 3 to 36 day administration period which is prior to or overlaps with the initial part of the administration period of said first pharmaceutical composition wherein said palliative pharmaceutical composition comprises a therapeutic agent, such as an acid suppressant, adapted for ulcer treatment.

BEST MODES OF CARRYING OUT THE INVENTION

Figure 1:
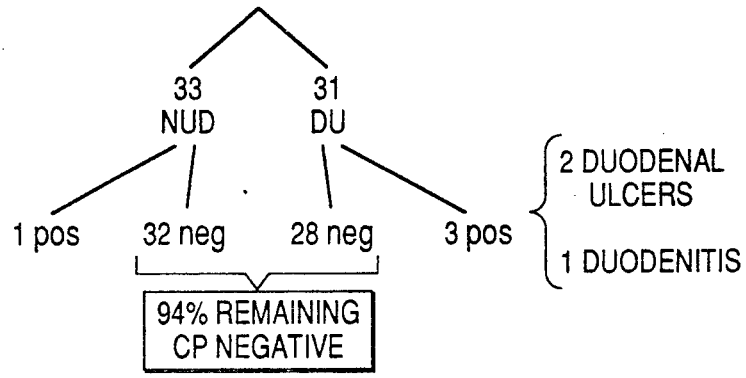
FIG. 1 illustrates results of treatment according to the present invention in 64 to 100 patients at an average of 19.3 months after treatment.

The methodology and treatment described above is useful in the treatment of disorders associated with *C. pylori* which include duodenal ulcer, pre-pyloric ulcer, gastric ulcer, oesophageal ulceration, reflux oesophagitis with or without ulceration, bile-reflux "gastritis" non ulcer dyspepsia associated with *C. pylori* gastritis and/or asymptomatic carrier state.

Whilst tablets or capsules of the pharmaceutical composition of the present invention are preferred, sachets or syrups or other orally ingestible forms of the compositions are also included within the scope of the present invention.

The invention will be further described with reference to the following test procedure of the Example and accompanying Figures.

EXAMPLE

Test Procedure

Patients aged 19 to 79 years (M:F=47:53) with symptoms of dyspepsia lasting three months or more referred for endoscopy, were entered. Only patients positive for *C. pylori* with either duodenal ulcer or non-ulcer dyspepsia were entered into the study. Patients were deemed to have non-ulcer dyspepsia if, in the absence of ulcer or other disease, they complained of food related epigastric discomfort or pain, bloating, belching, nausea, a feeling of fullness or heartburn. Patients with duodenal ulcer were entered into the treatment protocol only after ulcer treatment with either four weeks of ranitidine (300 mg/day) or cimetidine (800 mg/day), known not to influence *C. pylori*. Exclusion criteria included coagulopathy, antibiotic use within two weeks of endoscopy, presence of oesophageal varices, previous gastrectomy, neoplasm, systemic disease or allergy preventing use of the medications. Gastric ulcer patients were excluded to form a separate study. Of 122 patients entered in the study, 112 completed the triple chemotherapy adequately. Of these, 100 consecutive re-endoscoped patients became available for analysis of results at eight weeks after commencement of treatment and constitutes the short term follow up group. Ten patients did not complete the treatment due to failure to follow up (4), nausea (2), clostridium difficile-positive diarrhoea (1), allergy (2), and oral moniliasis (1). At 12 to 37 months after *C. pylori* eradication therapy CP-negative patient at eight weeks from the pilot studies and the abovementioned group were invited for re-examination by gastroscopy. Of the entire cohort 64 patients returned for examination and constitute the long term follow up group.

Gastroscopy

All examinations were carried out by the same endoscopist. Two biopsy specimens were taken from the gastric antrum and one from the body. One antral specimen was placed in a microtitre tray containing buffered urea and an indicator to detect rapidly presence of *C. pylori* urease activity. The other specimens were placed in 10% buffered formalin for histological examination. No bacterial cultures were carried out.

Histological Assessment

Paraffin sections of tissues fixed in formalin were stained with haematoxylin and eosin to grade severity of histological gastritis and with Warthin-Starry silver stain to grade *C. pylori* density. Grading was based on density of lymphocyte/plasma cell (chronic), neutrophil (active) infiltration, or presence of *C. pylori* from O to III as previously described.

Specimens were graded by the same consultant histopathologist without knowledge of patients' details.

Medication

Except for eight patients allergic to tetracycline, all subjects received a combination of colloid bismuth subcitrate (108 mg chew-tablets q.i.d.), tetracycline HCl (500 mg q.i.d.) for four weeks, together with metronidazole (200 mg q.i.d.) for the first ten days. Amoxicillin (500 mg q.i.d.) was substituted for tetracycline in the eight allergic patients. Patients and endoscopist were not blinded to the treatment regimen. Patients were asked if they had completed the medication as requested but no tablet count was attempted.

Assessment of Symptoms

For patients with idiopathic non-ulcer dyspepsia (NUD) a questionnaire form was developed and administered six months following clearance of *C. pylori*. Global assessment of percent improvement in these patients is reported below. In duodenal ulcer patients symptom improvement or disappearance was recorded.

RESULTS

Clearance of *C. pylori* at Eight Weeks

Of the 100 consecutive available patients treated for *C. pylori*, 94 were negative on urease testing and histology at eight weeks after commencement of chemotherapy (See Table 1). The six patients remaining positive at eight weeks claimed to have taken their medication as directed.

Long Term Clearance of *C. pylori*

Follow up gastroscopic biopsies were obtained in 64 patients (M:F=36:28) at 12 to 37 months after original triple chemotherapy (mean=19.3 months), and results shown in FIG. 1. These patients were drawn from the 94 who remained CP negative at eight weeks post therapy and from a small pilot study carried out some months earlier. Of these 64, paid recalled volunteers who resubmitted to gastroscopic biopsy, 33 had been originally diagnosed as having non-ulcer dyspepsia while 28 had endoscopically-proven duodenal ulcer. At follow up overall 60 or 94% remained free of *C. pylori* infection at the 19.3 months. One of the 33 NUD patients was again positive for the bacteria while three of 31 patients originally with duodenal ulcer were CP positive. In the latter three patients, two again had re-ulcerated while the other patient had pronounced duodenitis. All 28 patients who remained free of *C. pylori* maintained their ulcers endoscopically healed. They were on no maintenance therapy and were free of ulcer-like symptoms.

In NUD patients, as a global assessment in the 32 cleared patients, 25/32 (78%) reported a "50% or more improvement" over their initial symptom scores. On the other hand in four other patients with NUD in spite of CP eradication and reversal of histologic gastritis no improvement in dyspeptic symptoms occurred.

An unexpected finding in four of 15 patients who initially had linear oesophageal ulceration, was total healing and disappearance of the ulcers after C. pylori eradication. No appreciable weight change had occurred in these patients and the improvement could not be ascribed to any other medical therapy.

TABLE 1

| Patient | Age | M/F | C. pylori at start of treatment | C. pylori 8 wks past therapy |
|---|---|---|---|---|
| 1 N.U.D | 65 | F | +ve | −ve |
| 2 D.U | 59 | M | +ve | −ve |
| 3 N.U.D | 62 | F | +ve | −ve |
| 4 N.U.D | 63 | M | +ve | −ve |
| 5 N.U.D | 35 | M | +ve | −ve |
| 6 P.P.U | 74 | F | +ve | −ve |
| 7 G.U 3 | 40 | F | +ve | +ve* |
| 8 D.U | 65 | M | +ve | −ve |
| 9 2 D.U | 55 | F | +ve | −ve |
| 10 D.U | 60 | M | +ve | +ve* |
| 11 N.U.D | 60 | M | +ve | −ve |
| 12 N.U.D | 66 | M | +ve | −ve |
| 13 P.P.U | 59 | M | +ve | −ve |
| 14 N.U.D | 28 | F | +ve | −ve |
| 15 P.P.U | 36 | M | +ve | −ve |
| 16 D.U | 22 | M | +ve | −ve |
| 17 D.U | 42 | F | +ve | −ve |
| 18 N.U.D | 65 | F | +ve | −ve |
| 19 D.U | 32 | M | +ve | −ve |
| 20 D.U | 65 | M | +ve | −ve |
| 21 N.U.D | 61 | M | +ve | −ve |
| 22 D.U | 29 | F | +ve | +ve* |
| 23 N.U.D | 29 | M | +ve | −ve |
| 24 N.U.D | 30 | M | +ve | −ve |
| 25 D.U | 74 | M | +ve | −ve |
| 26 N.U.D | 42 | M | +ve | −ve |
| 27 N.U.D | 38 | M | +ve | +ve* |
| 28 P.P.U | 51 | F | +ve | −ve |
| 29 N.U.D | 26 | M | +ve | −ve |
| 30 D.U | 44 | F | +ve | −ve |
| 31 D.U | 50 | M | +ve | −ve |
| 32 N.U.D | 29 | F | +ve | −ve |
| 33 N.U.D | 72 | F | +ve | −ve |
| 34 N.U.D | 29 | M | +ve | −ve |
| 35 N.U.D | 22 | F | +ve | −ve |
| 36 D.U | 28 | M | +ve | −ve |
| 37 D.U | 54 | M | +ve | −ve |
| 38 N.U.D | 44 | F | +ve | −ve |
| 39 N.U.D | 56 | F | +ve | −ve |
| 40 N.U.D | 40 | M | +ve | −ve |
| 41 N.U.D |  | M | +ve | −ve |
| 42 N.U.D | 65 | F | +ve | −ve |
| 43 G.U/D.U | 53 | F | +ve | −ve |
| 44 N.U.D | 43 | M | +ve | −ve |
| 45 N.U.D | 73 | F | +ve | −ve |
| 46 N.U.D |  | F | +ve | −ve |
| 47 N.U.D | 46 | F | +ve | −ve |
| 48 N.U.D | 41 | M | +ve | −ve |
| 49 N.U.D | 46 | F | +ve | −ve |
| 50 N.U.D | 34 | M | +ve | −ve |
| 51 N.U.D | 58 | F | +ve | −ve |
| 52 N.U.D | 51 | F | +ve | −ve |
| 53 N.U.D | 23 | M | +ve | −ve |
| 54 N.U.D | 54 | F | +ve | −ve |
| 55 D.U | 59 | F | +ve | −ve |
| 56 P.P.U | 31 | M | +ve | −ve |
| 57 O.U | 56 | M | +ve | −ve |
| 58 N.U.D | 33 | M | −ve | −ve |
| 59 PREV G.U | 78 | M | +ve | −ve |
| 60 N.U.D | 63 | M | +ve | −ve |
| 61 N.U.D | 27 | M | +ve | −ve |
| 62 N.U.D | 45 | F | +ve | −ve |
| 63 N.U.D | 38 | M | +ve | −ve |
| 64 N.U.D | 36 | M | +ve | −ve |
| 65 N.U.D | 66 | F | +ve | −ve |
| 66 N.U.D | 70 | F | +ve | −ve |
| 67 P.P.U | 66 | F | +ve | −ve |
| 68 D.U | 37 | F | +ve | −ve |
| 69 N.U.D | 64 | M | +ve | −ve |
| 70 N.U.D | 45 | M | +ve | −ve |

TABLE 1-continued

| Patient | Age | M/F | C. pylori at start of treatment | C. pylori 8 wks past therapy |
|---|---|---|---|---|
| 71 N.U.D | 24 | F | +ve | −ve |
| 72 N.U.D | 46 | M | +ve | −ve |
| 73 N.U.D | 53 | F | +ve | −ve |
| 74 N.U.D | 33 | M | +ve | −ve |
| 75 N.U.D | 30 | M | +ve | −ve |
| 76 N.U.D | 42 | F | +ve | −ve |
| 77 D.U | 36 | M | +ve | −ve |
| 78 N.U.D | 64 | F | +ve | −ve |
| 79 D.U | 34 | M | +ve | −ve |
| 80 N.U.D | 65 | F | +ve | −ve |
| 81 N.U.D | 56 | M | +ve | +ve* |
| 82 N.U.D | 42 | M | +ve | −ve |
| 83 N.U D | 43 | F | +ve | −ve |
| 84 N.U.D | 75 | F | +ve | −ve |
| 85 N.U.D | 62 | F | +ve | −ve |
| 86 N.U.D | 64 | F | +ve | −ve |
| 87 N.U.D | 51 | M | +ve | −ve |
| 88 N.U.D | 39 | M | +ve | −ve |
| 89 N.U.D | 39 | F | +ve | −ve |
| 90 N.U.D | 40 | M | +ve | −ve |
| 91 N.U.D | 34 | F | +ve | −ve |
| 92 N.U.D | 60 | M | +ve | −ve |
| 93 N.U.D | 59 | M | +ve | −ve |
| 94 N.U.D | 67 | M | +ve | −ve |
| 95 N.U.D | 60 | F | +ve | −ve |
| 96 N.U.D | 38 | M | +ve | −ve |
| 97 N.U.D | 53 | M | +ve | +ve* |
| 98 N.U.D | 51 | M | +ve | −ve |
| 99 N.U.D | 54 | M | +ve | −ve |
| 100 N.U.D | 56 | M | +ve | −ve |

Figure 2:
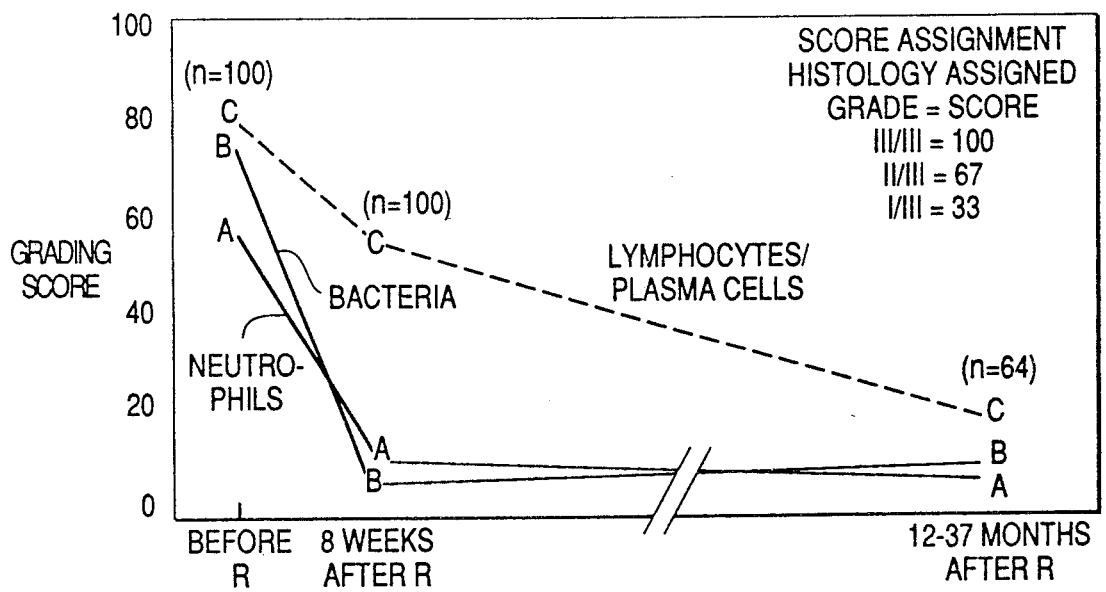
FIG. 2 illustrates histologic grading before and after treatment with the treatment of the present invention.

*indicates failure to cure infection.
D.U = Duodenal ulcer
O.U = Oesophageal ulcer
P.P.U = Pre-pyloric ulcer
G.U = Gastric ulcer
N.U.D = Non-ulcer dyspepsia Histological Changes The effects of therapy on histological grading of C. pylori density as well as lymphocyte and neutrophil infiltration are summarized in FIG. 2.

Histological scores have been arbitrarily assigned to show graphically the time-course of inflammation resolution. All patients presented initially with high scores for both chronic and active gastritis. Neutrophil infiltration disappeared rapidly parallelling C. pylori clearance. Lymphocyte infiltration, on the other hand, persisted for a much longer time.

This study has demonstrated that high (>90%) initial "clearance" of gastric C. pylori is possible with a combination of available antimicrobial agents. Such a high level of initial clearance has not been previously achieved. It is also clear that therapeutic success measure at the eight week biopsy, should for the present be termed "clearance". The term "eradication" should be reserved for patients remaining free of CP beyond six months. In this study most of those patients cleared of CP at eight weeks remained clear of the infection for more than twelve months.

Although C. pylori is susceptible to numerous antibiotics in vitro, such agents notoriously fail to eradicate it in vivo. Bismuth appears to be an important component in the combination chemotherapy. While it is not clear why several antimicrobials are required to improve eradication of CP, antibiotic access to the bacteria may be a problem. The bismuth compound may be required locally within the gastric pits and mucus whereas the antibiotics could be required to be carried systemically to reach bacteria deep in gastric pits and within endocytotic vacuoles. Presence of multiple strains of C. pylori with varying antibiotic susceptibility spectra could provide another explanation for the need to employ multiple antibiotics. In view of the multiplicity of strains, it is in fact surprising that such a high CP clearance rate could be achieved employing only two systemic antimicrobials and one locally-acting agent (CBS). Perhaps the success can be further explained by prevention of the development of resistant strains seen after short courses of single systemic antibiotics.

A clinically useful method for successful long term *C. pylori* eradication has not previously been described. Twelve month follow up figures of 51% and 35% have been reported using bismuth plus a single antibiotic. Such therapy would clearly be unsatisfactory for patients and may lead to creation of resistant *C. pylori* strains. It is also desirable to have an effective eradication therapy for *C. pylori* before embarking upon a double-blind trail designed to demonstrate the relevance of the organism in a particular disease.

Although it is known that bismuth can decrease tetracycline bioavailability, the antibiotic combination as used here achieved its desired effect in spite of presumed chelation. It would appear that adequate bismuth and tetracycline remained post-chelation to reach the infected targets. It is known also that chelation is in part pH dependent and low pH protects against chelation. As some patients with *C. pylori* infection will have impaired gastric acid secretion, elevated pH may have contributed to treatment failures. Other sources of treatment failure could include reduction in tetracycline bioavailability by ingestion of milk, antacids, iron or food, or simply non-compliance.

I claim:

1. A method of preventing recurrence of duodenal ulcer associated with *Campylobacter pylori* infection in a patient suffering from duodenal ulcer disease associated with *Campylobacter pylori* infection, said method comprising administering to said patient *Campylobacter pylori* infection eradicating amounts of pharmaceutically acceptable bismuth compound, first antibiotic selected from the group consisting of tetracycline and penicillins and second antibiotic which is metronidazole.

2. The method of claim 1 wherein said administering is to cause healing of duodenal ulcer as well as to prevent recurrence thereof.

3. A method of treating a patient with duodenal ulcer associated with *Campylobacter pylori* infection, said method comprising administering to said patient acid suppressant in an amount effective to obtain symptomatic relief and ulcer epithelialization before or during administering to said patient of *Campylobacter pylori* infection eradicating amounts of pharmaceutically acceptable bismuth compound, first antibiotic selected from the group consisting of tetracycline and penicillins and second antibiotic which is metronidazole, thereby to cause healing of said duodenal ulcer as well as to prevent recurrence thereof.

* * * * *